United States Patent [19]

Sparrow et al.

[11] Patent Number: 5,512,648
[45] Date of Patent: Apr. 30, 1996

[54] POLYAMIDE RESIN-PROTIDE CONJUGATE, PREPARATION AND USES

[75] Inventors: James T. Sparrow, 12119 Atwell, Houston, Tex. 77035; Nancy Kneib-Cordonier, Houston; Patrick Kanda; Robert E. Lanford, both of San Antonio, all of Tex.

[73] Assignees: James Sparrow, Houston; Patrick Kanda, San Antonio; Baylor College of Medicine, Houston, all of Tex.

[21] Appl. No.: 169,718

[22] Filed: Dec. 16, 1993

Related U.S. Application Data

[60] Division of Ser. No. 693,960, Apr. 29, 1991, Pat. No. 5,296,572, which is a continuation-in-part of Ser. No. 309,914, Feb. 10, 1989, Pat. No. 5,028,675, which is a continuation-in-part of Ser. No. 858,216, Apr. 30, 1986, abandoned.

[51] Int. Cl.$^6$ ................................................ C08F 226/02
[52] U.S. Cl. ........................... 526/307.3; 424/193.1; 436/518; 530/334; 530/402
[58] Field of Search .................. 525/54.1; 526/307.3; 424/193.1; 436/518; 530/334, 402

[56] References Cited

U.S. PATENT DOCUMENTS

| | | |
|---|---|---|
| 2,576,502 | 11/1951 | Dalton . |
| 2,656,339 | 10/1953 | Padbury . |
| 2,893,970 | 7/1959 | Caldwell et al. . |
| 3,032,539 | 5/1962 | Schuller et al. . |
| 3,057,833 | 10/1962 | Devlin . |
| 3,061,595 | 10/1962 | Dorion et al. . |
| 3,062,798 | 11/1963 | Lovett . |
| 3,912,607 | 10/1975 | Pierre et al. . |
| 3,925,267 | 12/1975 | Coupek et al. . |
| 4,074,039 | 2/1978 | Lim et al. . |
| 4,138,539 | 2/1979 | Landolt et al. . |
| 4,172,066 | 10/1979 | Zweigle et al. . |
| 4,504,640 | 3/1985 | Harada et al. . |
| 4,528,348 | 7/1985 | Turner et al. . |
| 4,658,000 | 4/1987 | Tyihak et al. . |
| 4,812,540 | 3/1989 | Kageno et al. . |
| 5,028,675 | 7/1991 | Kanda et al. . |

FOREIGN PATENT DOCUMENTS

| | | |
|---|---|---|
| 95233 | 11/1983 | European Pat. Off. . |
| 2123013 | 1/1984 | United Kingdom . |
| 2134531 | 8/1984 | United Kingdom . |

OTHER PUBLICATIONS

Atherton, E. et al., J. Amer. Chem. Soc. 97:6584 (1975).
Chersi, A. et al., J. of Immun. Methods, 122:285 (1989).
Fischer, P. et al., J. of Immun. Methods 118:119 (1989).
Takeyama, M. et al., Chem. Pharm. Bull., 37(3):834 (1989).
Gross, E. and Meienhofer, J., The Peptides: Analysis, Synthesis, Biology, 2:21 (1980).
Gutte, B. et al., J. of Bio. Chem. 246(6):1929 (1979).
Stahl, G. et al., J. Amer. Chem. Soc., 101:5383 (1979).

Primary Examiner—Joseph L. Schofer
Assistant Examiner—N. Sarofin
Attorney, Agent, or Firm—Ratner & Prestia

[57] ABSTRACT

A large pore polyamide resin is useful for large peptide and protein (protide) synthesis. A method of preparing the same comprises mixing a dimethylacrylamide monomer with an unsaturated or alkenoyl amine monomer, a cross-linker and water, homogeneously emulsifying the aqueous mixture with an organic solvent in the presence of an emulsifier, adjusting the pH of the aqueous mixture during polymerization to 6–8.5 to produce large pore resin beads, and isolating the beads. The beads may be used as a solid phase substrate for the synthesis of a polyamide/protide conjugate. The polyamide resin/protide conjugate may be used, without separation of the protide from the resin or subsequent purification, for immunizing mammals, including humans, against the protide, for affinity purifying immunological molecules binding to the protide, and for immunoassays.

21 Claims, No Drawings

POLYAMIDE RESIN-PROTIDE CONJUGATE, PREPARATION AND USES

This application is a divisional of 07/693,960, now U.S. Pat. No. 5,296,572 filed Apr. 29, 1991 which is a continuation-in-part of U.S. application Ser. No. 07/309,914, now U.S. Pat. No. 5,028,675 filed Feb. 10, 1989, by Patrick Kanda, Ronald C. Kennedy and James T. Sparrow, which was a continuation of U.S. application Ser. No. 06/858,216 now abandoned filed Apr. 30, 1986, by the same inventors entitled POLYAMIDE RESIN AND METHOD FOR PREPARATION OF REAGENTS FOR IMMUNODIAGNOSTIC USE. This invention was partially supported by NIH grant HL 27341.

BACKGROUND OF THE INVENTION

1. Field of the Invention

The present invention relates to a large pore resin useful for the synthesis of high MW peptides and proteins (protides) and conjugates thereof, and to the use of the resin/high MW protide conjugate to induce an immune response in experimental animals. More particularly, the present invention relates to a novel large pore polyacrylamide resin, a method of preparing the polyacrylamide resin, a resin/high MW protide conjugate, a method of preparing a resin/high MW protide conjugate, a method of inducing immune response in a mammal with the conjugate, and a method of using the resin/high MW protide conjugate for the affinity purification of antibodies and for immunodiagnostic purposes.

2. Description of the Background

Solid phase peptide synthesis is a valuable tool for investigating the structure and mechanism of action of proteins. Most such synthetic methods involve the use of cross-linked polystyrene resins as the solid phase to which the peptide is anchored during assembly, usually through a linker molecule. Assembly is accomplished by a repetitive cycle of adding a protected amino acid to the solid phase, selectively removing a protective group on that amino acid (deprotecting) and adding the next protected amino acid.

Although cross-linked, polystyrene resins have been used as supports in solid phase peptide synthesis, their relatively hydrophobic character in comparison to the polar organic media required to solubilize reactants can be problematic in peptide chain assembly. Such media may freely solvate a growing peptide, yet incompletely swell the polystyrene matrix. Within the polymer lattice, impaired diffusion of reagents and steric hindrance can contribute to lowered efficiency during coupling cycles, which, on a repeated basis, lowers final yields appreciably. During the early stages of assembly, when the resin to peptide mass ratio is high and the physical properties of the support dominate, this lowered efficiency is particularly acute.

Those shortcomings led to the development of a cross-linked, polydimethylacrylamide support which is highly polar in character and freely permeated by the requisite solvents for peptide synthesis. Such polyamide resin, as the aminomethyl derivative, permits the use of synthetic schemes incorporating alternate protection strategies through selection of appropriate linker molecules, which link C-terminal residues to the support. The thus synthesized peptide or protein, referred to herein as a "protide", may be used in a number of applications.

Of particular interest to the present invention is the use of a protide as an immunogen. It has previously been demonstrated that synthetic peptides analogous to sequences contained in vital-encoded proteins have proven useful for identifying native antigen determinants associated with such proteins, such as various HBsAg synthetic peptides. The induction of an antibody response to HBsAg, using such peptides, was proven to be relatively weak. However, this response could be enhanced through coupling of peptides to a carrier protein prior to immunization.

Moreover, the prediction of potential antigenic determinants of immunogenic proteins based on primary sequences analysis is far from being exact. Because of this, the identification of putative epitopes, through trial and error, may be laborious.

Affinity adsorbents have been prepared using commercially-available activated gels such as Bio-Gel P and Bio-Gel A (Bio-Rad), as well as conjugates of Sepharose or Agarose (Pharmacia) with low molecular weight substances. Polydimethylacrylamide resins have also been utilized as conjugates with small peptides for the purification of antibodies.

In addition, small peptide/polyamide resin conjugates were synthesized and utilized for the immunization of experimental animals. Previous technology permitted the synthesis on a solid polyamide resin support of amino acid sequences of limited length. In general, amino acid sequences of only up to twenty-five or thirty amino acids can be attained by previous methods.

There is still a need, therefore, for a method of preparing large synthetic peptides or proteins mimmicking native antigenic sequences which neither requires the purification of the synthetic peptide nor its coupling to a carrier protein.

SUMMARY OF THE INVENTION

This invention relates to a method of preparing a large pore polyamide resin that comprises mixing an unsaturated or alkenoyl amine monomer with a dimethylacrylamide monomer, a cross-linker and water in a proportion of monomer and cross-linker to water of about 1:2 to 1:50 (w/v);

adding an emulsifier in a volume proportion to the aqueous mixture of about 1:100 to 1:400;

adding an organic phase to the aqueous mixture;

agitating the aqueous mixture in the presence of the organic phase;

adding an initiator;

adjusting the pH of the aqueous mixture to about 6.0 to 7.5;

adding a promoter to start polymerization to obtain a polyamide resin bead of a pore size capable of lodging a protide of up to about 250,000 dalton MW; and isolating the thus formed polyamide resin bead.

This invention also relates to a large pore polyamide resin prepared by the method described above. The polyamide resin of the invention has a pore size such that it can lodge a protide of up to about 250,000 dalton MW, and in some instances even greater.

Also part of this invention is a method of preparing a polyamide resin/large protide conjugate that comprises preparing a large pore acrylamide resin by the method of this invention; and synthesizing an up to about 250,000 dalton MW protide on the resin.

This invention also relates to a polyamide/protide conjugate prepared by the method of the invention, where the protide may have a molecular weight of up to about 250,000 daltons, and even higher.

Also part of this invention is an immunizing composition that comprises the polyamide/protide conjugate of this invention; and a pharmaceutically-accepted diluent.

Also encompassed herein is a method of inducing an immunological response to a high MW protide in a mammal in need of such treatment comprising injecting into the mammal an amount of the resin/protide conjugate of this invention effective to elicit an immunological response to the protide.

This invention also relates to an in vitro immunoassay method that comprises contacting the resin/protide conjugate of this invention with a biological sample suspected of comprising a molecule having affinity and specificity for the protide portion of the conjugate;

allowing for the thus defined molecule present in the sample to bind to the conjugate; and detecting the presence of any molecule-bound resin/protide conjugate.

This invention also encompasses an immunoassay kit that comprises the polyamide resin of this invention;

amino acids and other reagents for conducting protide synthesis on the resin; and anti-human serum.

Also provided herein is an immunoassay kit that comprises the polyamide resin/protide conjugate described herein; and anti-human serum.

This invention also relates to a method of purifying a molecule having affinity and specificity for a protide from a biological sample, that comprises contacting the resin/protide conjugate of this invention with a sample comprising a molecule having affinity and specificity for the protide portion of the conjugate;

allowing for any thus defined molecule to bind to the conjugate;

separating the remaining sample from any resin/protide conjugate-bound molecule; and separating the resin/protide conjugate from any thus defined molecule.

These and other objects and advantages of the present invention will become clear to those skilled in the art from the following description.

DESCRIPTION OF THE PREFERRED EMBODIMENTS

This invention arose from a desire by the inventors to synthesize high molecular weight polypeptides or proteins (protides) on a solid phase such as a polyamide resin. The present invention provides technology that enables a partitioner to generate various pore size polyamide resin beads which are capable of lodging high MW protides, e.g., about up to 80,000 dalton, and even up to 250,000 dalton MW, and in many instances even higher MW.

The resin beads prepared in accordance with this invention have substantially large pores which can suitably accommodate protides such as antibody molecules, e.g., IgG molecules. This makes them extremely useful for applications such as affinity chromatography and the purification of antibody proteins or antipeptides. The resin beads prepared in accordance with this invention may be utilized to synthesize protides of molecular weights of up to 250,000 daltons, and in some instances even higher molecular weights, which may be cleaved off the resin and separated therefrom. The protide/polyamide resin conjugates are useful for the immunization of mammals, including humans, as well as for the production of immunoglobulins, such as IgG. In, addition, the conjugates may also be utilized to purify antibodies from the mammal's serum or other types of biological samples. Moreover, as already indicated, the polyamide resin/protide conjugate of the invention is also useful for the purification of any protein having affinity and specificity for an amino acid sequence contained in the protide, e.g., antibodies, antipeptides, receptors and the like.

This invention provides a method of preparing a large pore polyamide resin for the solid phase synthesis of high MW protides by polymerization of a dimethylacrylamide monomer, an unsaturated or alkenoyl amine monomer and a cross-linker in an aqueous medium. In a preferred embodiment, the proportion of unsaturated or alkenoyl amine monomer, dimethylacrylamide monomer and cross-linker to water is about 1:2 to 1:50, and is more preferably about 1:10 to 1:20(w/v). After the monomers, the cross-linker and the water are mixed, an organic phase is added to the aqueous mixture in a proportion of about 2.5:1.to 3.5:1, and more preferably about 3:1. The aqueous mixture is then agitated in the presence of the organic phase and an emulsifier in a preferred proportion of aqueous mixture to emulsifier of about 100:1 to 400:1, and more preferably about 200:1 to 300:1. To start polymerization a polymerization initiator is added. The pH of the aqueous mixture is adjusted to about 6.0 to 7.5, and more preferably to about 6.5 to 7.0. A promoter is added to obtain polyamide resin beads of a pore size capable of lodging a protide of up to about 250,000 dalton MW. The thus formed beads of polyamide resin may then be isolated by washing both organic and aqueous solvents away, and used as solid phase for the synthesis of a protide.

The polyamide resin of the present invention is prepared by cross-linking commercially available dimethylacrylamide monomers in aqueous solution using a cross-linker such as diaminoalkane, preferably a diaminoalkane having alkenoyl groups at either end of the molecule such as N,N'-bis-alkenoyldiaminoalkane. In a preferred embodiment of the invention, the cross-linker is either N,N'-bisacrylyl-1,3-diaminopropane or N,N'-bisacrylyl- 1,4-diaminobutane prepared according to the method of Halpern and Sparrow (Halpern, J. A., and Sparrow, J. T., Synthetic Comm.10:569(1980)), the relevant portion of the text of which is incorporated herein by reference.

The use of the propane analog (n=3) is particularly preferred over the ethyl analog because it yields a polymer of larger pore size and improved swelling properties during protide synthesis. However, it will be understood by those skilled in the art that other diaminoalkanes, such as N,N'-bisacrylyl-1,2-diaminoethane and N,N'-bisacrylyl-1,6-diaminohexane, are also appropriate for use in the preparation of the resin of the present invention.

A functional monomer is also included in the synthesis of the cross-linked resin of the present invention. The term "functional monomer" refers to those aminoalkenes and N-alkenoyldiaminoalkanes, which are used to anchor the C-terminal amino acid of a synthetic protide to the resin. The functional monomer may be protected with a methylsulfonylethyloxycarbonyl (MSC) group (Tesser, G. I., and Balvert-Geers, I. C., Int.J. Peptide Protein Res.7:295(1975), in order to prevent reaction of the free amino group during polymerization. The functional monomers may be prepared by reaction of commercially available chloride derivatives of MSC with the aminoalkene or N-alkenoyldiaminoalkane to form a urethane. The urethane, in the case of allylamine, is readily purified, e.g., by passage through silicic acid in chloroform, and crystallized in plates from, e.g., methylene chloride:hexane, and the MSC protective group may subsequently be removed with base.

The MSC-protected functional monomer is found in general to be completely soluble in the aqueous solution containing the other polymerization monomers. However, the MSC group is not required if the pH is sufficiently acidic to maintain the amino group of the functional monomer in a protonated state, i.e., a pH between 6.0 and 7.0.

The amount of functional monomer added is selected to yield a resin substitution of between about 0.1 mmol and about 0.7 mmol per gram of resin, and preferably in the range of about 0.2 to 0.7 mmol/g resin. For instance, loadings of about 0.2–0.4 mEq/g resin were realized when the level of MSC-allylamine was increased to 20 mole %. The initiator may be any of the initiators known to those skilled in the art such as a persulfate or riboflavin, and is preferably ammonium persulfate.

In a most preferred embodiment, the proportion of cross-linker to dimethylacrylamide comprises about 1:4 to 1:50, and more preferably about 1:8 to 1:25.

In a preferred embodiment of the present invention, the functional monomer is an N-acrylyldiaminoalkane.

The proportion of water added to the monomers and cross-linker is critical for the formation of large pores in the polymer beads. A higher proportion of water produces larger pores as can be seen from the exemplary disclosure provided below. Typically, the proportion of water to total amount of monomer and cross-linker is about 2:1 to 50:1, and more preferably about 5:1 to 20:1.

Because the above-described substances are combined in an aqueous medium, they are collectively referred to as "the aqueous phase" or "aqueous mixture". The aqueous phase is thereafter added with an organic phase. The term "organic phase" refers to an organic solvent which, when combined with the aqueous phase and stirred, results in a suspension from which the resin of the present invention may be obtained. In a preferred embodiment, the organic phase comprises a mixture of hexane and carbon tetrachloride in various proportions. However, other solvents may also be utilized.

The proportion of aqueous phase to organic phase is typically about 1:2.5 to 1:8 by volume, and more preferably about 1:3 to 1:6 by volume. However, other ratios may also be utilized.

An emulsifier is also added. The emulsifier may be any detergent known to those skilled in the art. In a preferred embodiment, the emulsifier comprises sorbitan sesquioleate, sorbitan monolaurate, sorbitan monodecanoate, or mixtures thereof. The amount of emulsifier added is adjusted to give a spherical resin of approximately uniform size.

Typically, the proportion of emulsifier to aqueous phase or mixture is about 1:100 to 1:400, and more preferably about 1:200 to 1:300 by volume. A decrease in the amount of detergent below this range may result in an emulsion which yields increased amounts of larger, amorphous material, which could contribute to a reduction in the length of the internal growing amino acid chains. An increase in the amount of detergent above this range may increase the amount of fine material, which is difficult to remove without the loss of significant amounts of the resin. Those fines may clog the reaction vessels of the peptide synthesizer as well as the associated lines and valves.

A solution of promoter titrated to pH between 6.0 and 7.5 may be added to promote the polymerization of the monomers in suspension, resulting in the formation of beads of the polyamide resin. Alternatively the pH of the aqueous mixture may be adjusted separately as well as the promoter and initiator added separately. A number of promoters are known to those skilled in the art, but particular success in preparing the polyamide resin of the present invention has been obtained with N,N,N',N'-tetramethylethylene-diamine (TEMED).

In a preferred method of preparing the resin, the pH of the promoter solution is adjusted prior to polymerization with dilute mineral acid to about 6.0, but acceptable resins have been prepared at a pH of about 6.0 to about 7.5.

The resulting beads may then be filtered and washed, the MSC group, if present, removed with base, and the beads dried for storage. The beads may then be sifted through a mesh or sieve to insure their relatively uniform size. The Overall yield of the resin prepared using the method of the present invention may be as high as about 87% to 94% based on the starting monomers, and in some cases even higher.

The cross-linked polydimethylacrylamide resin of the invention, therefore, takes the following general structure, depending upon the identity of the functional monomer.

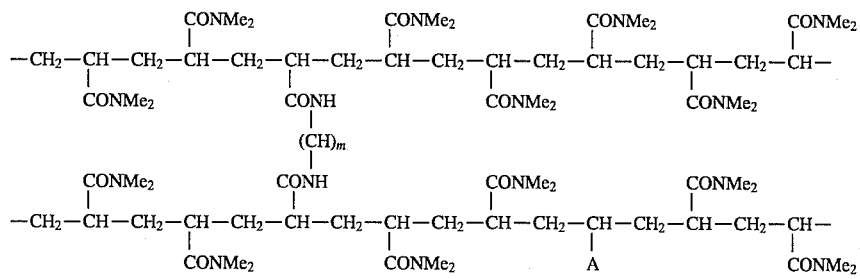

The presently preferred integer is 1 when allylamine is used as the functional monomer when A is either $-(CH_2)_y-NH_2 \cdot HCl$ in the case of an aminoalkane wherein x is an integer, or $-CONH-(CH_2)-_y NH_2 \cdot HCl$ when it is an N-alkenoyl-aminoalkane functional monomer where y is an integer and 6 when N-acrylyl-1,6-diaminohexane is used as the functional monomer and n is an integer. The preferred integer n is either 3 or 4 when either N,N'-bisacrylyl-1,3-diaminopropane or N,N'-bisacrylyl-1,4-diaminobutane are used as the cross-linker.

Also provided herein is a conjugate comprising the polyamide resin of the invention and an about 800 to 250,000 dalton MW protide. The conjugate is prepared by a method provided herein. The method comprises preparing a large pore polyamide resin as described above and then synthesizing an up to about 250,000 dalton MW protide thereon. The synthesis of the protide on the resin is conducted by implementing technology known in the art.

The term "protide", as used herein, refers to peptides and proteins of high molecular weight which are synthesized according to the method of the present invention. Protides of MW higher than about 20,000 or 30,000 dalton MW could not be synthesized previously.

This structure provides maximum exposure of a protide in a polar organic or aqueous solution, and the resin-polymer backbone does not restrict the protide conformationally. The exposure of the protide is the result of the ability of the polyamide resin to swell to many times its dry bed volume when highly solvated by a polar organic solvent or water.

Briefly, a protide is coupled to a polystyrene based resin for solid phase synthesis through a benzyl ester derivative. The separation of the completed protide from the resin is usually accomplished by either acidic or basic cleavage. Benzyl esters are susceptible to several such methods of cleavage, but are also stable throughout the multiple deprotection, neutralization and coupling reactions which are characteristic of solid phase synthetic methods. Hydrazine has also been used to separate the protide from the resin (Kessler, W., and Iselin, S., Helv.Chim.Acta 49:1330(1966)) as have various ammonolytic (Manning, M., J.Am. Chem. Soc.93:1348(1968)), and other methods. These methods, however, require that appropriate steps be taken to avoid damage to the protide resulting from cleavage followed by purification of the protide from the by-products of the synthesis, including amino acids, short peptides, decomposition products of the resin, and sometimes, peptides containing incompletely removed protecting groups.

Purification may in many instances be accomplished by direct crystallization. Where the contaminating peptides are of a size and composition similar to that of the desired product, however, more selective techniques must be employed. Regardless of the method of separation and purification, those requirements add time-consuming steps to the synthesis, which often lowers the total yield of protide. The method of the present invention requires no such separation and/or purification and, thereby, decreases the length of time required to complete the synthesis of the protide while increasing its yield.

A protide may then be synthesized on the beads by direct coupling to the resin or by coupling through a linker which is attached to the resin with an activator. The term "linker" refers to a linking group which links the carboxyl group of the first amino acid of the protide to the polymeric resin. In a preferred embodiment, this linker comprises an oxyalkyl benzoic acid (OBA) having one or more amino acid residues coupled thereto to serve as the first amino acids in the protide chain. Because the OBA linker is used to attach the C-terminal amino acid of the first amino acid to the polyamide resin of the present invention, anhydrous hydrogen fluoride may be used to remove the side chain protecting groups from the protide without significant loss of the protide from the resin.

In the examples provided below, the first amino acid of choice is glycine, which is protected with a t-butyloxycarbonyl (t-Boc) protecting group, but it will be understood by those skilled in the art that the amino acid could be any amino acid, such as the amino acid which is the first amino acid in the protide to be synthesized. Other protecting groups are equally suitable, as well. A short chain of amino acids may also be used which function as a spacer between the protide and the resin-polymer backbone. Polyglycine is one such chain of amino acids which may be so used, as well as polyalanine. For synthesis of more complex protides, i.e., those which are comprised of multiple chains, or when it is desired to synthesize multiple epitopes as may be the case for synthetic protide antigens, a short chain of amino acids may be used which will accommodate synthesis along two linear sequences. The short chain of amino acids of choice for such a synthesis, especially when the protide to be synthesized includes one or more lysine residues, has the following formula.

u-lys-v

In this formula, u is either (1) the amino acid residue adjacent the N-terminus of lysine in the sequence of the protide to be synthesized, or (2) if it is not desired to synthesize a protide which includes the lysine residue, u is alanine, glycine, or other readily available, preferably charge neutral, amino acid. v is glycine, alanine, or other electrically neutral amino acid which is readily commercially available.

In the event it is desired to synthesize multiple epitopes or multiple chain synthetic protides using the short chain of amino acids, synthesis is accomplished through the ε-N of lysine as follows.

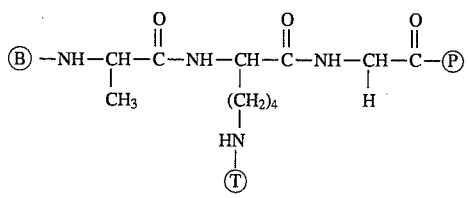

In this formula, B is the first synthetic protide to be synthesized, T is the second synthetic protide to be synthesized, and P is the remainder of the polymerized resin. For example, T and B could represent T-cell and B-cell epitopes, respectively, for inducing an immune response in an animal. Those skilled in the art will recognize that lysine is but one of several amino acids having an amino group in the side chain such that synthesis of the protide T can be accomplished on the amino acid sidechain. Other such amino acids include ornithine, asparagine, glutamine, arginine, histidine, 5-hydroxylysine, desmosine, isodesmosine, and citrulline. The amino acids lysine, ornithine, and 5-hydroxylysine are, however, preferred because of their lack of electrical charge, absence of steric hindrance as a result of their relatively small side chains, and lack of any stabilizing double bonds which increase the difficulty of protecting and/or deprotecting the side chain amino group.

It will also be understood by those skilled in the art that lysine or another residue having an amino group within the side chain may be coupled directly to the resin or the OBA linker without the u and v amino acid residues. Either way, the resin is effectively double loaded such that it is possible to synthesize two protides from the same point of anchorage to the resin. The resin may also be used to synthesize two of the same protides simultaneously by, for instance, synthesizing the u-lys-v tripeptide with the Boc protecting group on the ε amino group of the lysine residue. The α amino group of the u amino acid may then be protected with a fluorenylmethyloxycarbonyl (Fmoc) protecting group, the ε amino group of the Boc-protected lysine residue is deprotected, and an amino acid substituted onto the ε amino group. The Fmoc protecting group may then be removed from the α amino acid, both unprotected amino acids contacted with the appropriately protected first amino acid in the protide to be synthesized, and synthesis continued as is known to those skilled in the art by repetitive deblocking, selective activation, and addition of amino acids in the desired sequence.

In the event it is desired to synthesize different protides at the same anchorage site, it may be necessary to use both Fmoc and Boc protecting groups. Further, additional protecting groups, stable to both Fmoc-based and Boc-based synthetic schemes, must be utilized. For instance, if it is desired to add lysine to the chain on which Fmoc-based schemes are being used, Fmoc and cbz (on the ε amino group) protecting groups are used, the cbz group being stable to both Fmoc and Boc chemistry. Selection of appropriate protecting groups in this fashion is generally within the skill of an artisan.

The method of this invention permits the synthesis of protides of about 800 to up to about 80,000 dalton MW, optionally up to about 120,000 dalton MW, and in some instances up to about 250,000 dalton MW and even higher. By varying the proportion of water and emulsifier to monomers and cross-linker in the aqueous mixture, polymers of different pore size are obtained.

Boc-glycyl-4-(oxymethyl) benzoic acid is the preferred linker disclosed herein. It may be prepared by a modification of the method described by Mitchell, et al. (Mitchell, et al., J.Org.Chem.43:2845(1978)), the portion of the text which is necessary to enable the method being incorporated herein by reference. The Mitchell method was modified by eliminating the use of dimethylformamide as a solvent because it is difficult to evaporate. Even though evaporation may be accelerated by elevating the temperature, the prior art method is still time-consuming. The 4-(bromomethyl)-benzoic acid phenyl ester linker may be converted to the boc-glycyl derivative by reaction with the tetramethyl-ammonium (TMA) salt of Boc-glycine.

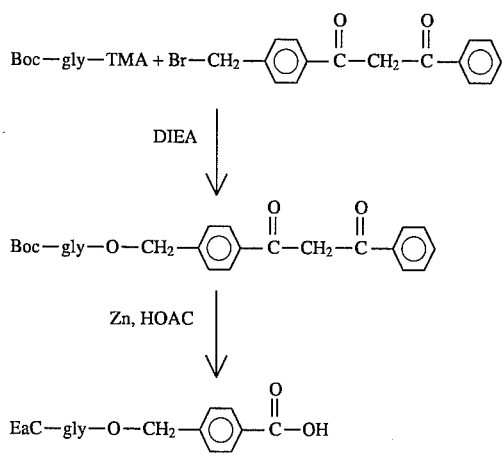

The phenacyl ester may be reductively cleaved with zinc in 85% acetic acid to give Boc-glycyl-(4-oxymethyl) benzoic acid with an overall yield of about 85% and sometimes higher.

The activators used in the examples to couple the linker to the polyamide resin prepared as described above are diisopropyl carbodiimide and 4-dimethylaminopyridine. It will, however, be understood by those skilled in the art that other activators such as dicyclohexylcarbodiimide (DCC) and 4-methylpyrrolidinopyridine, among others, are equally suitable for such a purpose. For instance, the Boc-glycyl-(4-oxymethyl) benzoic acid may be anchored to the aminomethyl polydimethylacrylamide resin using DCC activation with 4-dimethylaminopyridine (DMAP) as catalyst.

Also provided herein is a method of preparing a polyamide resin/large protide conjugate that comprises preparing a large pore polyamide resin by the method of this invention as was described above; and synthesizing an up to about 250,000 dalton molecular weight protide on the resin by methods known in the art.

Also provided herein is a polyamide resin/about 800 to 250,000 dalton MW protide conjugate prepared by the method described above. In a preferred embodiment of the invention, the polyamide resin/protide conjugate comprises a protide of about 10,000 to 200,000 dalton MW, and more preferably about 50,000 to 180,000 dalton MW.

An immunizing composition is also provided herein which comprises the polyamide resin/high MW protide conjugate of this invention; and a pharmaceutically-acceptable diluent.

The immunizing composition described herein may comprise different amounts of the conjugate with respect to the diluent. Typically, an amount of polyamide resin/protide conjugate containing about 1.0 to 20 mg of the protide will be combined with about 1 ml of diluent, and more preferably an amount of conjugate comprising 2.0 to 10 mg of protide per ml of diluent. Pharmaceutically-acceptable diluents are known in the art and need not be described herein. In a further preferred embodiment, the immunizing composition further comprises an adjuvant. Suitable adjuvants are known in the art and will not be described herein. The adjuvant is added in amounts which are standard in the art.

The polyamide resin/high MW protide conjugate of this invention may be used for a number of purposes, including in vitro assays, inducing an immunogenic response in mammals (immunization) such as humans, purification of immunological molecules having affinity and specificity for the high MW protide, and the like.

Also provided herein is an in vitro immunoassay, that comprises contacting the resin/high MW protide conjugate of this invention with a biological sample suspected of comprising a molecule having affinity and specificity for the protide portion of the conjugate;

allowing for any thus defined molecule present in the sample to bind to the conjugate; and detecting the presence of any molecule-bound resin/protide conjugate.

In a preferred embodiment of the invention the method further comprises binding or adsorbing the polyamide resin/high MW protide conjugate to a solid support prior to the contacting step. And in still another preferred embodiment, the detecting step comprises radioimmuno-detection or enzyme/substrate assaying. For instance, an in vitro assay may be conducted by crushing the beaded polyamide resin/high MW protide conjugate with mortar and pestle, and absorbing the crushed conjugate onto a solid phase such as a microtiter test plate with neutral pH buffer. Serum or other body fluid or biological sample suspected of containing an antibody capable of specifically binding the high MW protein or peptide bound to the resin may then be incubated with the absorbed conjugate, unbound antibodies removed by washing, and the bound antibodies detected by an enzyme-linked immunosorbent assay, biotin-avidin amplified assay or other detection methods such as radioimmunoassays which are known in the art.

Also provided herein is an immunoassay kit for practicing the immunoassay of the invention described above. In one preferred embodiment, the kit comprises the large pore polyamide resin of this invention;

amino acids and other reagents for conducting protide synthesis on the resin; and anti-human serum.

In another preferred embodiment the immunoassay kit comprises the already prepared polyamide resin/high MW protide conjugate of the invention; and anti-human serum.

The anti-human serum may be radioactively labeled prior to use or it may be coupled to a specialized enzyme and used, e.g., as an enzyme-bound immunoglobulin.

Still another part of this invention relates to a method of purifying a molecule having affinity and specificity for a protide from a biological sample, the method comprising contacting the resin/high MW protide conjugate of the invention with a sample comprising a molecule that has affinity and specificity for the protide portion of the conjugate;

allowing for any thus defined molecule to bind to the conjugate;

separating the remaining sample from any resin/high MW protide conjugate-bound molecule; and separating the resin/high MW protide conjugate from any thus defined molecule.

The methods of the invention may be conducted without any separation and purification steps required by other synthetic methods.

In another embodiment, the conjugate may be crushed and absorbed to a solid support such as a microtiter test plate and the presence of antibodies in a sample assayed as described above. Separation of the protide from the resin and purification of the protide is generally not required for such an assay.

The polyamide resin/high MW large protide conjugate is also useful as an immunogen. The conjugate may be used directly for immunization with or without an adjuvant. For instance, an immune response specific for hepatitis B, as measured by radioimmunoassay, may be induced by immunization of a mammal, including humans, with a conjugate comprising a high MW synthetic peptide comprising the amino acid sequence of the hepatitis B surface antigen (HBsAG) peptide 119–159 emulsified in Freund's complete adjuvant. Similarly, immunization may be attained by injection of a conjugate comprising a high MW peptide corresponding to a large portion of the protein coat of the AIDS virus HTLV-III and the large pore polyamide resin of the invention, a conjugate comprising the inventive resin and a high FEW peptide homologous to a rat fatty acid binding protein, a large pore resin/high MW peptide conjugate of the invention comprising a long amino acid sequence homologous to the predicted sequence of the Abelson murine leukemia virus (ABL), and/or a large pore polyamide resin/high MW peptide conjugate in which the peptide is homologous to a high MW protein fragment of apolipoproteins B and/or C.

Immunization may be conducted with varying amounts of the conjugate. Typically, an amount of conjugate comprising about 50 to 200 μg/Kg body weight may be given in a single dose, and preferably about 65 to 120 μg/Kg body weight.

Repeated immunizations may be administered to boost the effect.

The present invention will be better understood by reference to the following examples, which are presented for purposes of exemplification only and are not belied to provide a limitation to the present invention.

EXAMPLES

Example 1: Preparation of Allylamine Functional Monomer

Five grams (26.8 mmol) 2-methylsulfonyl ethyloxycarbonyl chloride (MSC chloride) (K+K Labs, ICN) were dissolved in 15 ml acetonitrile and added dropwise over a 20 minute period to a stirred solution of 2.1 ml (28 mmol) redistilled allylamine (Kodak) and 4.9 ml (28 mmol) redistilled diisopropylethylamine (DIEA) in 20 ml acetonitrile. The DIEA (Aldrich) was refluxed over ninhydrin and redistilled. The solution was stirred an additional 2 hours and the solvent evaporated. The residue was taken up in 250 ml ethyl acetate and allowed to stand for one to two hours. The bulk of the DIEA hydrochloride salt precipitated as needles. After filtration and evaporation, the crude material was dissolved in a minimal amount of chloroform and loaded onto 60 g of a G-60 silica gel column packed in the same solvent. Elution with chloroform yielded pure MSC-allylamine. $R_F$ on TLC= 0.64 (Solvent=$CHCl_3$ : $CH_3OH$, 9:1).

The remaining DIEA salts were absorbed to the column under these conditions. Occasionally, material migrating near the solvent front on TLC contaminated the MSC-allylamine column fractions. That material was removed by crystallizing the MSC allylamine from methylene chloride-hexane at −20° C. The yield was 4.8 g (86% from MSC chloride).

Example 2: Preparation of Cross-linker

The cross-linker N,N'-bisacrylyl-1,3-diaminopropane was prepared according to the method of Helpern and Sparrow, supra. Briefly, diaminopropane (Aldrich) was dissolved in acetonitrile and added dropwise to an acrylyl chloride-acetonitrile solution at 4° C., allowed to warm to room temperature and stirred. The diaminopropane dihydrochloride was removed by filtration, washed with warm acetonitrile, and the combined filtrates were concentrated in vacuo. N,N'-bisacrylyl-1,3-diaminopropane was crystallized at 4° C. overnight and the resulting plates filtered and dried in vacuo.

Example 3: Preparation of Polydimethylacrylamide Resin

In a 2-liter cylindrical, fluted polymerization glass vessel fitted with a nitrogen inlet and mechanically driven glass stirrer were added 490 ml hexane and 290 ml carbon tetrachloride. The solution was purged for 15 minutes with nitrogen to remove oxygen. An aqueous solution containing 2.9 grams (15.9 mmol) N,N'-bisacrylyl-1,3-diaminopropane prepared as described in Example 2 mixed with 18.2 ml (175 mmol) N,N-dimethylacrylamide (PolySciences) were added. 10 g (48 mmol) MSC allylamine prepared as described in Example 1 and 120 ml water were added, and the solution was filtered and degassed before addition to the organic phase. The density of the resulting mixture was adjusted to obtain a uniform suspension with stirring at 400–450 RPM. 0.5 g ammonium persulfate (BioRad) in 5 ml $H_2O$ and 1 ml of either sorbitan sesquioleate or sorbitan monolaurate (Sigma) were then added. A solution of 3 ml N,N,N',N'-tetramethylethylenediamine (TEMED) (BioRad) in 2 ml H$_2$O, pH 6.5–7.5 (conc. HCl) was then added to the suspension and the suspended emulsion was stirred for 2 hours under nitrogen atmosphere.

The resulting beaded material was then filtered and washed sequentially with water (one liter) methanol (one liter), a mixture of dioxane:methanol: 2N NaOH (14:5:1, 2 liters, to remove MSC group), water (2 liters), 1N HCl (2 liters), water (2 liters), and then methanol (2 liters). The resin was de-fined by suspension in methanol and decanting (3×). After swelling in methylene chloride (Baker HPLC grade), the resin was shrunk in hexane and dried in vacuo. Large amorphous material was removed by sifting the resin through an 80 mesh (180 micron) sieve.

The degree of functionalization was checked by coupling Boc-alanine to 100 mg of the resin using diisopropylcarbodiimide as activator and 4-dimethylaminopyridine recrystallized from ethyl acetate as catalyst. Amino acid analysis showed a substitution of 0.15 to 0.35 mmol/g resin depending on the lot. Resins were prepared with about 0.1 to 0.5 mmol/g resin depending upon the amount of allylamine added. The loaded resin gave no detectable staining with picryl-sulfonic acid, indicating the absence of unreacted free amine. When swollen in methylene chloride, the beads occupied about 2.5 times their dry bed volume. When swollen in dimethylformamide or an aqueous solution, the beads occupied approximately four and six times their dry bed volume, respectively.

Example 4: Preparation of Aminohexyl Resin

A solution of 600 ml of carbon tetrachloride and 1070 ml of hexane were placed in a flask and stirred under nitrogen at about 600 rpm. A solution of 73 g dimethylacrylamide (Poly Sciences), 11.2 g N,N-bisacryloyl-1,2-diaminopropane, and 18.16 g N-acryloyl-1,6-diaminohexane HCl in 500 ml cold water were added to the organic solution. The density adjusted by adding hexane or carbon tetrachloride until the aqueous solution stayed suspended when the stirrer was stopped. 2 g ammonium persulfate dissolved in 2 ml water were then added, followed by about 1 ml of sorbitan laurate and a solution of 6 ml of TEMED in 6 ml of water pH 6.0 (12N HCl). Polymerization was allowed to proceed for about 3 hours, after which time the stirrer was stopped, hexane was added, the resin allowed to settle, and the organics removed by aspiration.

The resin was transferred to a 3 liter filter funnel, washed in methanol, water, and methanol, resuspended in methanol, and allowed to settle, and fine material was removed from the methanol by aspiration. The resin was washed with 3×2 l dimethylformamide and methylene chloride, stirred and then washed with ethylacetate and hexane. The resin was then dried in a vacuum dessicator and passed through an ASTM 80 mesh screen to obtain about 93 grams of resin. After neutralizing with 100 ml of 1N sodium hydroxide per gram of resin, washing with water, methanol, and methylene chloride, the loading was determined by amino acid analysis to be 0.7 mEq/g after coupling Boc-alanine to the resin.

Example 5: Preparation of Linker

The linker Boc-glycyl-4-(oxymethyl) benzoic acid was prepared by a modification of the method of Mitchell, et al., supra. Briefly, 4-(bromomethyl) benzoic acid phenylacylester was prepared by dissolving 10.3 ml redistilled diisopropylethylamine and 12.05 g (60.6 mmol) bromoacetophenone in 450 ml ethyl acetate. 13.89 g (60.6 mmol) 4-(bromomethyl) benzoic acid were added in seven equal portions over a 3 hour period to the stirred solution at 40°–50° C. Stirring was continued for 2 more hours at room temperature. Precipitated Et$_3$N.HBr was removed by filtration and the ethyl acetate solution was washed four times with 50 ml each of an aqueous solution of 10% citric acid, saturated sodium chloride, saturated sodium bicarbonate, and saturated sodium chloride. The organic phase was dried over anhydrous magnesium sulfate and freed of solvent by rotary evaporation under reduced pressure. The residue was crystallized from CH$_2$Cl$_2$-petroleum ether (1:3 v/v) to give the 4-(bromomethyl) benzoic acid phenacylester.

4-(bromomethyl) benzoic acid phenylacylester was converted to Boc-glycyl-4-(oxymethyl) benzoic acid by dissolving 25 mmol (4.38 g) Boc-L-glycine in 15 ml methanol and titrating to neutrality with 25% tetramethyl-ammonium hydroxide in methanol. The solvent was removed azeotropically with chloroform in vacuo, and the salt was dissolved in 150 ml acetonitrile. To the stirred solution were added 5.8 g (17.5 mmol) 4-(bromomethyl) benzoic acid phenacyl ester prepared as described. After overnight mixing, the precipitated tetramethylammonium bromide was filtered and the solvent evaporated. The residue was dissolved in 400 ml ethyl acetate and the solution filtered.

The organic phase was then washed successively with 10% aqueous citric acid (3×75 ml), 0.5M sodium bicarbonate:0.5M potassium carbonate (2:1) pH 9.5 (8× 75 ml), and then water (3×75 ml). The solution was dried with MgSO$_4$, and the solvent removed in vacuo. The residue was dissolved in 200 ml 85% acetic acid to which 23 g acid washed zinc dust were added. The mixture was stirred until the phenacyl ester was no longer visible by TLC, about 4 to 5 hours. The zinc dust was filtered out and washed with 50 ml acetic acid, and the combined solutions were lyophilized. The residue was suspended in 100 ml water:300 ml ethyl acetate, and the pH adjusted to 1.5 with concentrated HCl. The aqueous layer was extracted with a second portion of 200 ml ethyl acetate and the combined extracts were washed with 100 ml water. After drying with MgSO$_4$ and evaporating, the Boc-glycyl-4(oxymethyl) benzoic acid was purified by recrystallization from methylene chloride:hexane at −10°. The yield was 4.5 g (14.5 mmol, 83% from the phenacyl ester).

Example 6: Coupling of Linker to Polyamide Resin

Boc-glycyl-4-(oxymethyl) benzoic acid prepared as described in Example 5 was coupled to 1.2 g aminomethyl polyamide resin prepared as described in Example 3, as well as the aminohexyl resin prepared as described in Example 4, on a Biosearch Sam II automated peptide synthesizer using diisopropylcarbodiimide and dimethylaminopyridine as activator in a 1:1 methylene chloride:dimethylformamide solution. Both methylene chloride (Baker HPLC grade) and dimethylformamide (Baker Photrex grade) were used without further purification.

Following treatment with hydrogen fluoride, 50 mg of the glycyl resin prepared as described in Example 3 were found to contain 0.13 mmol/g of linker by amino acid analysis. Amino acid analysis was performed using a Beckman Model 119 amino acid analyzer following either 2 hour hydrolysis (12N HCl:propionic acid, 1:1, 135° C.) or 24 hour hydrolysis (6N HCl, 110° C.) of resin-bound peptides.

Example 7: Synthesis of Hepatitis B Antigen Peptide

The hepatitis B surface antigen (HBsAg) peptide 119–159 was assembled on the aminomethyl, cross-linked polydimethylacrylamide resin prepared as described in Example 3, having the Boc-glycyl-4-(oxymethyl) benzoic acid linker prepared as described in Example 5 attached thereto using the method described in Example 6, with all residues being double coupled using a Biosearch Sam II automated peptide synthesizer. The sequence of that HBsAg peptide is as follows relative to the AYW subtype.

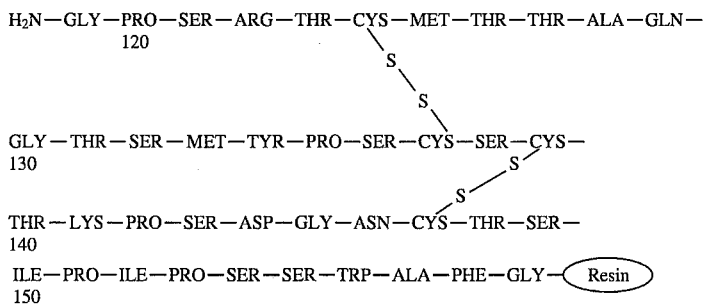

The peptide included the following substitutions to control the specific formation of disulfide loops. Serines substituted for cysteines 121, 138, and 149. The cysteines 139 and 147 sulfhydryls were blocked by the 4-methoxybenzyl group, while the sulfhydryls of the cysteines at 124 and 137 were protected as the S-acetamidomethyl derivatives. α-N-tBoc protected amino acids were purchased from Bachem. Additional side chain protecting groups were as follows: formyl group for the indole nitrogen of tryptophan; benzylethers for threonine and serine hydroxyls; acetamidomethyl or 4-methoxybenzyl for cysteine sulfhydryls as described above; benzyl esters for β-carboxyl of aspartic acid and the γ-carboxyl of glutamic acid; 2-chlorobenzyloxycarbonyl for ε-amino group of lysine; 2,6-dichlorobenzyl ether for the phenolic hydroxyl of tyrosine; and the p-tosyl group for the guanidine of arginine. For the synthesis, methylene chloride (Baker HPLC grade) and DMF (Baker Photrex grade) were used without further purification. Diisopropylethylamine (DIEA) (Aldrich) was refluxed over ninhydrin and redistilled. Trifluoroacetic acid (Halocarbon) was redistilled, with the middle cut used in deblocking steps. All other chemicals were reagent grade or better and used without further purification.

Side chain protecting groups were removed from the completed peptidyl-resin by treatment with anhydrous HF (20 ml/g resin) at 0° for 30 minutes, containing 10% anisole and 2% ethanedithiol. Following evaporation of HF, the peptidyl-resin was washed successively with ether, 1% acetic acid, methanol, 5% DIEA in methylene chloride, methanol, then water. The peptidyl-resin was dried in vacuo. The formyl group was removed from the tryptophan by treatment with 1M ethanolamine at 0°. A disulfide bridge was formed between cysteines 139 and 147 by potassium ferricyanide treatment. A second disulfide bridge between cysteines 124 and 137 resulted during simultaneous removal of the acetamidomethyl moieties with a solution of iodine in acetic acid.

Example 8: In Vitro Assay for Presence of HBsAg Antibody

Human serum is assayed for the presence of antibody specific for the HBsAg peptide 119–159 by the following in vitro assay. A quantity of the HBsAg peptide 119–159-polyamide resin conjugate prepared as described in Example 6 was crushed with mortar and pestle. A microscope was used to verify that the polyamide resin-peptide conjugate was crushed. Approximately 100 μl of a solution containing about 200 nanograms to 10 micrograms of crushed polyamide resin-peptide conjugate in a neutral pH buffer such as phosphate buffered saline (PBS) was absorbed to a solid phase such as Dynatech Immunolon II Microtiter test plates. Nonspecific binding sites were blocked with 10% normal goat serum (NGtS) and the plate was washed with Tween 20 PBS (T-PBS) to remove unbound antibodies.

Human sera suspected of containing antibodies specific for HBsAg peptide 119–159 and rabbit antisera produced by immunizing rabbits with the polyamide resin-HBsAg peptide 119–159 conjugate diluted in 10% NGtS were then added to the polyamide resin-peptide-coated plate and incubated for 1 hour at 37° C., followed by washing with T-PBS. Biotin goat anti-human IgG or biotin goat anti-rabbit IgG (Vector Laboratories, Burlingame, Calif.) was then incubated with the bound human and rabbit sera, respectively, for 1 hour at 37° C. The wells were washed and avidin conjugated to horseradish peroxidase (Av-HRP) was added for 20 minutes at room temperature. The wells were then washed with T-PBS to remove any unbound Av-HRP, and peroxidase activity was determined using a 1 mM solution of 1,2'-azinodi(3-ethylbenzthiazoline sulfonic acid) (Sigma Chemical Co.) and 0.03% $H_2O_2$ as substrate. The reaction was stopped with 5% (w/v) sodium dodecyl sulfate in water prior to spectrophotometric quantitation at 410 nm using a Dynatech plate reader. Optimal dilutions of each reagent were selected by titration. All reagents for determining specific binding except the substrate were diluted in 10% NGtS.

Example 9: In Vitro Assay for Presence of HBsAg Antibody

Human serum was assayed for the presence of antibody to hepatitis B surface antigen by the following in vitro assay. A 10% solution of the polyamide resin-HBsAg peptide 119–159 conjugate was prepared in a buffered bovine serum albumin (BSA) solution containing a final concentration of 40% tetrahydrofuran. An equal volume of antibody specific for the HBsAg peptide 119–159 containing about 100,000 to 1,000,000 counts per minute $I^{125}$ were added and incubated with gentle rocking. The resulting suspension was centrifuged and the pellet washed with 1% BSA-Tween 20 PBS, and then centrifuged again. The radioactivity of the pellet was then counted in a Gamma counter. The results clearly indicate the recognition of the polyamide resin-HbsAg peptide 119–159 conjugate by native HBsAg antibody.

TABLE 1

In Vitro Assay of HBsAg Antibody

| Sample | Glycyl resin (Control) | Resin-HBsAg peptide 119–159 conjugate |
|---|---|---|
| IgG Human anti-HB1 | 1240 cpm* | 22,840 |
| IgG Human anti-HB2 | 1921 | 28,732 |
| Normal human IgG | 1432 | 1,949 |

*all measurements in counts per minute

Example 10: Use of Polyamide Resin Protide Conjugate to Induce an Immunogenic Response in Mammals The polyamide resin-peptide conjugate prepared as described in Example 7 was used to induce an immunogenic response in rabbits as follows. New Zealand white female rabbits were immunized with three monthly intramuscular injections of either 200 μg HBsAg peptide 119–159 as the peptide/resin conjugate, or only glycyl-resin emulsified in Freund's complete adjuvant. A range of immunogen of about 50 μg to 1 mg was used for rabbits. Serum was collected after bi-weekly bleeding and checked for anti-HBsAg activity using a commercially available radioimmunoassay (RIA) kit (AUSAB, Abbott Laboratories). The recognition of the native HBsAg surface antigen by the anti-peptide 119–159 antibody response induced in the rabbits is demonstrated by the following data developed by that RIA.

TABLE 2

Immunization with Different Immunizers

| | Rabbit Immunogen | Immunization | Antibody Titer[a] (RIA units/ml) |
|---|---|---|---|
| 1 | Glycine-Resin | Preimmune[a] | ≦8[b] |
| | | Primary | ≦8 |
| | | Secondary | ≦8 |
| | | Tertiary | ≦8 |
| 2 | HBsAg Peptide-Resin | Preimmune | ≦8 |
| | | Primary | ≦8 |
| | | Secondary | 183 |
| | | Tertiary | 920 |
| 3 | HBsAg Peptide-Resin | Preimmune | ≦8 |
| | | Primary | ≦8 |
| | | Secondary | 72 |
| | | Tertiary | 262 |

[a]Sera obtained prior to immunization.
[b]Antibody titer to HBsAg is below the sensitivity of the RIA kit and is considered not to contain specific antibodies.

As can be seen from these data, the polyamide resin-HBsAg peptide 119–159 conjugate containing a single disulfide bridge between cysteines 139 and 147, when used to immunize rabbits, yieldes anti-peptide antisera which cross reactes with HBsAg.

Example 11: Synthesis of HTLV-III Antigen Peptide

The amino acid sequence between residue numbers 503–532 of the gp120 HTLV-III envelope glycoprotein was assembled on the cross-linked polydimethylacrylamide resin prepared as described in Example 3 where the Boc-glycyl-4-(oxymethyl) benzoic acid linker was prepared as described in Example 5 and attached thereto using the method of Example 6, in the same method as described for the synthesis of the HBsAG peptide 119–159 in Example 7, the only difference being the order in which the protected amino acids were added. The sequence of amino acids 503–532 of the gp120 HTLV-III peptide is as follows.

gp.120 503–532

$H_2N$—VAL—ALA—PRO—THR—LYS—ALA—LYS—ARG—ARG—
503

VAL—VAL—GLN—ARG—GLU—LYS—ARG—ALA—VAL—GLY—

ILE—GLY—ALA—LEU—PHE—LEU—GLY—PHE—LEU—

GLY—ALA—GLY—O—CH$_2$—⌬—C(=O)—N(H)—CH$_2$—(RESIN)
532

Using the same method, three additional peptide-resin conjugates have been prepared which include the following amino acid sequences which are homologous to portions of the envelope glycoprotein of HTLV-III, each identified by their respective residue numbers.

TABLE 3

Sequencer Utilized

| Sequence | Homologous to |
|---|---|
| 304–327 | gp120 |
| 341–370 | gp120 |
| 733–756 | gp41 |

Example 12: Ability of HTLV-III Peptide/Resin Conjugates to Bind to Human anti-HIV Antibodies HTLV-III is one of several strains of retrovirus which have been implicated as the causative agent of human Acquired Immunodeficiency Syndrome, or AIDS, all of which are referred to as Human Immunodeficiency Virus, or HIV. To test the immunogenicity of the peptide/resin conjugate of the present invention, 4 conjugates having peptides homologous to portions of the HTLV-III envelope glycoprotein prepared as described in Example 11 were tested against serum samples taken from 110 HIV-infected humans for their ability to bind anti-HIV antibodies. That assay was conducted as follows.

2 μg samples of each conjugate were absorbed to Dynatech Immunolon microtiter test plates in borate buffered saline (BBS) pH 8.2 overnight at 4° C.

Non-specific sites were blocked with 200 μl 10% normal goat serum (NGtS) in Tween 20-phosphate buffered saline (T-PBS) for 20 minutes at room temperature and then washed three times with T-PBS. Biotin goat anti-human IgG (Vector Laboratories, Burlingame, Calif.) was then incubated with the bound human sera for 1 hour at 37° C. Wells were washed 3 times and avidin conjugated to horseradish peroxidase (Av-HRP) was added for 20 minutes at room temperature. The wells were again washed 3 times with T-PBS and peroxidase activity determined using a 1mM solution of 1,2'-azino-di(ethyl-benzthiazolinesulfonic acid) (Sigma Chemical Co.) with 0.03% $H_2O_2$ as the substrate. The reaction was stopped with 5% (w/v) sodium dodecyl sulfate in water and optical density read at 410 nm using a Dynatech plate reader. Optimal dilutions were selected by titration.

The results were as shown in Table 4 below. A positive result was defined as an optical density three standard deviations above the mean optical density obtained with 20 seronegative samples.

TABLE 4

| Peptide Sequences Used that Bound h-antibodies | | |
|---|---|---|
| Peptide Sequence | Individuals | Positive |
| 304–327 | 26 | 24 |
| 341–370 | 33 | 30 |
| 503–532 | 44 | 40 |
| 733–756 | 24 | 22 |

Example 13: Use of Polyamide Resin/HTLV III Synthetic Peptide Conjugate To Induce an Immunogenic Response Rabbits immunized with the polyamide resin/HTLV-III peptide 503–532 conjugate produced a specific anti-peptide response as determined by an enzyme linked immunosorbent assay conducted according to the method of Examples 8 with the use of antisera produced by immunization of rabbits with the polyamide resin/HTLV-III peptide 503–532 conjugate rather than the conjugate including the HBsAg peptide 119–159 used in that Example, and in Example 12. The results of the immunoassay are presented graphically in FIG. 1. The data represented by the circles is data from rabbits immunized with that conjugate, the data represented by triangles is from those same rabbits before immunization. The solid circles and triangles are from one rabbit and the open circles and triangles are from a second rabbit. A conjugate comprised of the polyamide resin and a third peptide failed to demonstrate significant binding. One of the rabbits produced an anti-HTLV-III response specific for the HTLV-III gp120 envelope protein based on a radioimmunoprecipitation assay conducted according to the method of Allan and Barin (Allan, J. S., et al., Science 228:1091 (1985); Barin, F., et al., Science 228:1094 (1985)), portion of which are incorporated herein in their entirety by reference to the extent necessary for enablement.

The ability of rabbit antisera against peptide 503–532 to neutralize HTLV-III infectivity was assessed on the basis of a reduction of reverse transcriptase activity using a tenfold dilution of the HTLV-III stock with a constant amount of antisera (Barre-Sinoussi, F., et al., Science 220:868 (1983)). A single rabbit anti-peptide 503–532 antiserum efficiently reduced HTLV-III replication at day 10 compared to pooled human sera from AIDS patients at tenfold dilutions of virus. A second rabbit antiserum to that peptide failed to reduce HTLV-III replication and so was used as a control throughout the RT assay. No anti-HTLV-III activity was detected in this particular antiserum based on radioimmunoprecipitation even though the rabbit received a similar immunogen and produced a detectable anti-peptide response.

The antiserum that neutralized HTLV-III detected both gp120 and gp160 envelope glycoproteins. This rabbit antiserum was found to be less efficient in neutralizing HTLV-III compared to human AIDS serum on day 12 and 15 following HTLV-III infection.

Example 14; Production of Antibodies Using Peptide/Resin Conjugates

To further test the immunogenicity of the peptide-resin conjugates of the present invention, 4 additional peptide-resin conjugates were prepared, injected into rabbits, and their sera tested for the presence of antibody against the respective native proteins. Those peptide-resin conjugates were prepared in the same manner as set out in Example 7, and included the following peptides.

(a) A peptide having a sequence homologous to a portion of the amino acid sequence of the rat fatty acid binding protein residue numbers 22–34 (FABP) (Chan, L., et al., J. Biol. Chem. 260:2629 (1985)).

(b) A peptide having a sequence homologous to a portion of the predicted amino acid sequence of the murine Abelson leukemia virus (abl 389–403; Reddy, E., et at., Proc. Nat'l. Acad. Sci. USA 80:3617(1983)).

(c) A peptide having a sequence homologous to a portion of the amino acid sequence of the apolipoprotein C-II, residue numbers 56–69 (Apo C-II) (Hospattanker, A. V., et al., J. Biol. Chem. 260:318 (1984)).

(d) a peptide having a sequence homologous to a portion of the amino acid sequence of the apolipo protein B, residue numbers 3357–3369 (Apo B) (Yang, C.-Y., et al., Nature 323:738 (1986)).

Peptides were coupled directly to the aminohexyl resin prepared as described in Example 4 containing 0.70 mM glycine per gram resin for synthesis. Once synthesis was completed, the resins were dried and 0.5 g of each resin sample was treated with 10 ml anhydrous HF containing 10% anisole and 1% ethanedithiol for 30 minutes at 0° C. HF was evaporated under vacuum at 0° C. and the resin transferred to a glass filter funnel with ether, washed with 3×50 ml each of ether, methanol, water, 1% acetic acid, water, 0.1M Tris, water, 1% acetic acid and water to neutrality, and then dried in a vacuum dessicator. The amino acid composition of each sample was determined by hydrolysis with 12N HCl:propionic acid (1:1) at 135° C. for 2 hours and analyzed on a Beckman 6300 amino acid analyzer. Amino acid sequences of each peptide were determined with either an Applied Biosystems Model 470A or 477A protein sequencer.

Samples of each peptidyl-resin (1 mg) were swollen in 100 μl of sterile normal saline and crushed with an homogenizer. After mixing with an equal volume of incomplete Freund's adjuvant, the mixtures were injected into New Zealand white rabbits at multiple sites. After 2 weeks, serum was obtained from an ear vein and checked with an ELISA test for antibody against the native protein. Rabbits were then boosted with mixtures prepared in this same manner and the process repeated over two months. Antibody titers after 2 months, determined against native proteins (not the respective peptide) were as shown in Table 5 below.

TABLE 5

Antibody Production

| Peptide | Antibody Titer |
| --- | --- |
| FABP | 900 |
| ABL-389 | 64 |
| Apo C-II | 250 |
| Apo B | 50 |

The experiment was repeated after synthesizing a T-cell epitope from *Staph. aureus* nuclease having the following amino acid sequence.

lys-met-val-glu-asp-ala-lys

The T-cell epitope was added synthetically to the amino terminal of the remaining peptidyl-resin conjugate for each of the peptides, viz., FABP, ABL-389, Apo C-II, and Apo B. The remaining steps were repeated exactly as above. The following antibody titers were found.

TABLE 6

Antibody Titers

| Peptide | Antibody Titer |
| --- | --- |
| FABP | 2500 |
| ABL-389 | 2550 |
| Apo C-II | 1250 |
| Apo B | 250 |

In a second set of tests, the ABL-resin and FABP resin conjugates were ground in a tight-fit homogenizer with 20 strokes, and 500 µg of the ground conjugate was suspended in 1.5 ml of phosphate buffered saline (PBS) and emulsified with another 1.5 ml of Freund's complete adjuvant. The rabbits were injected subcutaneously at multiple sites, and two booster injections of each PBS-conjugate suspension in Freund's incomplete adjuvant were given at 2 week intervals. Two weeks after the second booster, the rabbits were bled and anti-peptide titer assayed in an ELISA test against the respective peptide of the resin-peptide conjugate.

The ELISA test was conducted by plating 50 ng of each peptide in 0.1M $NaHCO_3$ pH 9 in the wells of a 96-well test plate and drying overnight at 37° C. Non-specific sites were blocked with a TN solution of 50 mM Tris-HCl pH 7.6 and 50 mM NaCl with 5% non-fat dry milk for 1 hour at 37° C. 50 µl sera were added in serial dilution to each well and incubated at 37° C. for 1 hour. The plates were washed 6 times with TN solution containing 0.05% Tween 10 (Sigma). 50 µl of peroxidase-conjugated goat anti-rabbit IgG (1:4000) (Boehringer Mannheim Biochemicals) in TN buffer with 5% nonfat dry milk were added to each well, and after incubating for 1 hour, plates were washed six times with TN solution. 50 µl of o-phenylene-diamine (OPD) (Sigma) were added to each well as substrate and incubated for 20 minutes at room temperature.

The plates were read at 495 nm in an ELISA autoreader as a net value in which the optical density (OD) reading of the pre-immune sera was subtracted from the OD of the immune sera. Optical density is plotted as a function of serum concentration in FIG. 2. Each data point represents the average of three rabbits. The circles represent the data from rabbits immunized with the ABL-resin conjugate and the triangle represents data from rabbits immunized with the FABP-resin conjugate.

Example 15: Preparation of Aminohexyl Polydimethylacrylamide Resin with Pores Accepting 40,000 Dalton MW Proteins Polydimethylacrylamide resin beads containing an aminohexyl group was prepared as follows in a siliconized 3-liter indented, cylindrical polymerization glass vessel (Reliance Glass) fitted with a nitrogen inlet and mechanically drived siliconized glass propeller-type stirrer. 554 ml of hexane and 346 ml of carbon tetrachloride were added to the vessel. The solution was purged for 15 min with nitrogen to remove oxygen. A cold aqueous solution containing 2.5 g (13.7 mmol) N,N'-bisacrylyl-1,3-diaminopropane, 18.2 g (184 mmol) N,N-dimethyl-acrylamide, 4.54 g (22 mmol) N-acrylyl-1,6-diaminohexane hydrochloride monomers and 250 ml cold water was prepared. This solution was filtered and degassed and then added to the organic phase. The density of the aqueous/organic mixture was adjusted by addition of hexane or carbon tetrachloride to obtain a uniform suspension of the aqueous phase. 0.5 g Ammonium persulfate in 1 ml $H_2O$ and 1.6 ml sorbitan monolaurate were added while stirring at 400–450 rpm. A solution of 1.5 ml N,N,N',N'-tetramethylethylenediamine (TEMED) in 1.5 ml $H_2O$ pH 6.5 (conc. HCl) was then added after ensuring an appropriate droplet size.

Polymerization commenced after about 30 to 45 minutes and stirring was continued for 3 to 4 hours under a nitrogen atmosphere. Hexane was then added, stirring stopped and the beaded resin allowed to settle. The supernate was removed with suction and the beaded material filtered on a 3 l siliconized glass funnel and washed sequentially with methanol (2×1 l), water (2×1 l) and methanol (2×1 l). The resin was de-fined by suspension in 1 l methanol, allowed to settle and any suspended material removed by decantation.

This process was repeated 3 times. Washing was concluded with methylene chloride (3×1.5 l), ethyl acetate (1×1.5 l) and hexane (2×1 l), and the resin was then dried in vacuo. Any large amorphous material was removed by sifting the resin through an 80 mesh (180 micron) sieve. Overall yields were up to about 90 to 99%.

The degree of functionalization was confirmed by neutralizing 3 g of aminohexyl hydrochloride resin with 1N NaOH and then washing with water, methanol, and methylene chloride. Boc-glycine was coupled as the symmetric anhydride formed with dicyclohexylcarbodiimide and catalyzed with 4-dimethylaminopyridine recrystallized from ethyl acetate. Amino acid analysis showed a substitution of about 0.5 to 0.7 mmol/g resin, depending on the lot. The loaded resin gave no detectable staining with picrylsulfonic acid, indicating the absence of unreacted free amine.

The pore size of the Boc-glycyl resin was determined by washing 3 g of the resin on a siliconized funnel with methanol, water, and 0.01M sodium phosphate buffer pH 7.4, transferring to a siliconized filter flask, degassing and placing it in a 0.9×28 cm column. Mixtures of peptides and proteins of known molecular weights were then loaded onto the column and eluted with phosphate buffer. The elution profile and the log molecular weight v. elution volume are not shown but were obtained. From these profiles, the pore size was estimated to be large enough to accommodate a protein of molecular weight 40,000 Daltons.

Example 16: Preparation of Aminohexyl Polydimethylacrylamide Resin with Pores Accepting 80,000 Dalton MW Proteins A resin was prepared as above except that the monomers were dissolved in 375 ml cold water and suspended in 433 ml of carbon tetrachloride and 693 ml hexane at a stirring speed of 495 rpm. 0.5 g ammonium persulfate in 1 ml water and then 1.2 ml sorbitan monolaurate were added to obtain a desirable droplet size. The polymerization was allowed to proceed for 3.5 hours, and the beaded resin was then washed as above and loaded in the same manner with Boc-glycine. The loading was 0.63 mmol/g.

After washing and preparing a column of the resin, the pore size of the Boc-glycyl resin was determined in the manner described above. The elution profile and the log molecular weight v. elution volume are not shown but were obtained. The pore size of the resin was estimated therefrom to be large enough to accommodate up to about an 80,000 Dalton MW protein.

Example 17: Preparation of Aminohexyl Polydimethylacrylamide Resin with Pores Accepting 120,000 Dalton MW Proteins A resin was prepared as above except that the monomers were dissolved in 500 ml of cold water and suspended in 519 ml of carbon tetrachloride and 831 ml hexane at a stirring speed of 570 rpm. 0.5 g ammonium persulfate in 1 ml of water, and then 1.3 ml sorbitan monolaurate were added to obtain a desirable droplet size. The polymerization was allowed to proceed for about 3.5 hours, and the beaded resin was washed as above and loaded in the same manner with Boc-glycine. The loading was 0.27 mmol/g.

After washing and preparing a column of the resin, the pore size of the Boc-glycyl resin was determined in the manner described above. The elution and the log molecular weight v. elution volume profiles are not shown but indicate that a protein of up to 120,000 Daltons MW can be accommodated by the resin.

Example 18: Preparation of Aminohexyl Polydimethylacrylamide Resin with Pores Accepting 250,000 Dalton MW Proteins A resin was prepared as above except that the monomers were dissolved in 500 ml cold water and suspended in 519 ml carbon tetrachloride and 831 ml hexane with stirring at 500 rpm. 0.5 g ammonium persulfate in 1 ml of water, and then 1.4 ml sorbitan monolaurate were added to obtain an appropriate droplet size. After the polymerization was allowed to proceed for 3.5 hours, the beaded resin was washed as above and loaded in the same manner with Boc-glycine. The loading was 0.42 mmol/g.

After washing and preparing a column of the resin, the pore size of the Boc-glycyl resin was determined in the manner described above. The elution profile and the log molecular weight v. elution volume plot (not shown) indicate a protein of 250,000 Daltons MW can enter the pores of the resin.

Example 19: Preparation of Rabbit-antibodies against WT Nuclear Transport Signal Peptide A synthetic peptide was conjugated to keyhole limpet hemocyanin (KLH) using the heterobifunctional crosslinker MBS. The conjugate was repeatedly injected into rabbits as an emulsion containing Freund's incomplete adjuvant. Serum was obtained after the 4th. and 5th. injections. IgG was prepared by removal of albumin by caprylic acid precipitation, followed by ammonium sulfate precipitation of IgG. The precipitated IgG was resuspended in PBS and dialyzed.

Example 20: Immunopurification of Rabbit Anti-WT Nuclear Transport Signal Peptide on a Peptide Bound Resin 0.12 mg of peptide resin were swollen in phosphate buffer saline (PBS) that contains 100 uM leupeptin and 1 mM PMSF.

The resin was packed into a small column and the column washed with 25 ml of PBS at a flow rate of 15 ml per hour. 27.5 mg of IgG in 13 ml rabbit anti-peptide IgG were applied to the column and circulated through the column overnight with the aid of a peristaltic pump. The column was washed with 25 ml PBS, 25 ml PBS+1M NaCl, and then with 25 ml PBS.

The bound IgG was slowly eluted with 15 ml of ammonium thiocyanate. Each 1 ml fractions were collected and the optical density (OD) of each fraction at 280 nm was determined. Peak fractions were then dialyzed against PBS.

The amount of starting IgG, unbound IgG, and affinity purified IgG were determined by an ELISA assay after layering them on wells previously coated with BSA-SPDP-WT peptide or keyhole limpet hemocyanin (KLH).

Example 21: ELISA Assay

Microtiter wells were incubated with 200 ng of BSA-SPDP-peptide or KLH, incubated overnight in PBS, and then blocked with PBS containing 10% NGS for 30 minutes at 37° C. The microtiter wells were washed 3 times with PBS containing 0.3% Tween and then incubated for 1 hour at 37° C. with rabbit anti-peptide IgG at different concentrations in PBS containing 10% NGS. The wells were washed 3 times with PBS containing 0.3% Tween and then incubated for 1 hour at 37° C. with goat anti-rabbit IgG conjugated with horse radish peroxidase diluted in PBS containing 10% NGS. The wells were washed 3 times with PBS containing 0.3% Tween and incubated with a peroxidase substrate 2,2'-azino-bis (3-ethylbenzthiazoline) sulfonic acid for 30 minutes at 23° C. The optical density of the samples was read at 410 nm.

TABLE 7

ELISA Results

| ug IgG/well | Start | Unbound or Flow Through | Affinity Purified |
|---|---|---|---|
| | P/N Ratio $\frac{\text{(OD BSA-SPDP-Peptide)}}{\text{(OD KLH)}}$ | | |
| 125 ug | $.90 \frac{(827)}{(924)}$ | $.85 \frac{(810)}{(954)}$ | $1.83 \frac{(800)}{(438)}$ |
| 31.3 | $.82 \frac{(700)}{(852)}$ | $.75 \frac{(636)}{(846)}$ | $2.60 \frac{(692)}{(266)}$ |
| 7.8 | $.74 \frac{(588)}{(800)}$ | $.62 \frac{(497)}{(802)}$ | $3.14 \frac{(562)}{(179)}$ |
| 1.9 | $.60 \frac{(433)}{(719)}$ | $.50 \frac{(362)}{(726)}$ | $4.37 \frac{(450)}{(103)}$ |

Each row represents the results of successive passages of the unbound, or flow-through fractions through the column, resulting in progressively greater binding specificity of the fractions for the peptide vs. KLH.

The invention now being fully described, it will be apparent to one of ordinary skill in the art that many changes and modifications can be made thereto without departing from the spirit or scope of the invention as set forth herein.

We claim:

1. A method of preparing a resin/large MW protide conjugate, comprising preparing a large pore polyamide resin by mixing an unsaturated or alkenoyl amine monomer with a dimethylacrylamide monomer, a cross-linker and water in a proportion of monomer and cross-linker to water of about 1:2 to 1:50 (w/v);

adding an emulsifier in a proportion to the aqueous mixture of about 1:100 to 1:400, adding an organic phase to the aqueous mixture;

agitating the aqueous mixture in the presence of the organic phase, adding an initiator;

adjusting the pH of the aqueous mixture to about 6.0 to 7.5;

adding a promoter to start polymerization to obtain polyamide resin beads of a pore size capable of lodging a protide of up to about 250,000 dalton MW;

isolating the thus formed polyamide resin beads; and synthesizing an up to about 250 Kdalton MW protide on the resin.

2. A polyamide protide conjugate prepared by the method of claim 1.

3. An composition, comprising the polyamide/protide conjugate of claim 2; and a diluent.

4. The immunizing composition of claim 3, further comprising an adjuvant.

5. An immunoassay kit, comprising a large pore polyamide resin prepared by mixing an unsaturated or alkenoyl amine monomer with a dimethylacrylamide monomer, a cross-linker and water in a proportion of monomer and cross-linker to water of about 1:2 to 1:50 (w/v), adding an emulsifier in a proportion to the aqueous mixture of about 1:100 to 1:400, adding an organic phase to the aqueous mixture, agitating the aqueous mixture in the presence of the organic phase, adding an initiator, adjusting the pH of the aqueous mixture to about 6.0 to 7.5, adding a promoter to start polymerization to obtain polyamide resin beads of a pore size capable of lodging a protide of up to about 250,000 dalton MW, and isolating the thus formed polyamide resin beads;

amino acids and other reagents for conducting peptide synthesis on the resin; and anti-human serum.

6. An immunoassay kit, comprising the polyamide resin/protide conjugate of claim 2; and anti-human serum.

7. A method of purifying a molecule having affinity and specificity for a protide from a biological sample, comprising contacting the resin/protide conjugate of claim 1 with a sample comprising a molecule having affinity and specificity for the protide portion of the conjugate;

allowing for any thus defined molecule to bind to the conjugate;

separating the remaining sample from any resin/protide conjugate-bound molecule; and separating the resin/protide conjugate from any thus defined molecule.

8. The method of claim 7, wherein the molecule comprises an antibody.

9. The method of claim 1, wherein the alkenoylamine monomer comprises an allylamine monomer.

10. The method of claim 9, wherein the allylamine monomer comprises an N-alkenoyl-diaminoalkane.

11. The method of claims 1, wherein the crosslinker comprises a diaminolkane.

12. The method of claim 11, wherein the diaminoalkane comprises a N,N'-bisalkenoyl-diaminoalkane.

13. The method of claim 12, wherein the N,N'-bisalkenoyl-diaminoalkane is selected from the group consisting of N,N'-bisalkenoyl-1,3-diaminopropane;

N,N'-bisalkenoyl-1,3-diaminoethane;

N,N'-bisalkenoyl-1,3-diaminobutane; and

N,N'-bisalkenoyl-1,3-diaminohexane.

14. The method of claim 1, wherein the allylamine monomer carries a protective group.

15. The method of claim 14, further comprising removing the allylamine protective group from the polyamide resin by contacting the beads with a base.

16. The method of claim 14, wherein the allylamine protective group comprises methysulfonylethyloxycarbonyl.

17. The method of claim 1, wherein the organic phase comprises a mixture of hexane and carbon tetrachloride; and the emulsifier is selected from the group consisting of sorbitan monolaureate, sorbitan decanoate, and sorbitan sesquiolate.

18. The method of claim 1, wherein the beads are isolated by filtering, washing and drying.

19. The method of claim 1, further comprising coupling a linker to the polyamide resin beads.

20. The method of claim 1, wherein the proportion of cross-linker to dimethylacrylamide comprises about 1:4 to 1:50.

21. The composition of claim 3, wherein the diluent comprises a pharmaceutically-acceptable diluent.

* * * * *

UNITED STATES PATENT AND TRADEMARK OFFICE
CERTIFICATE OF CORRECTION

PATENT NO. : 5,512,648
DATED : April 30, 1996
INVENTOR(S) : James T. Sparrow et al.

It is certified that error appears in the above-indentified patent and that said Letters Patent is hereby corrected as shown below:

Column 2, line 2, before "proteins" change "vital" into --viral--.

Column 4, line 10, after "In" delete the --,--.

Column 7, line 29, after "Iselin," delete "S" and insert --B--.

Column 8, line 3, delete "chain-of" and insert --chain of--.

Column 9, line 57, beginning of formula, delete "EaC" and insert --Eo$^c$--.

Column 11, line 56, after "high" delete "FEW" and insert --MW--.

Column 21, line 58, before "Mannheim" delete "(Bochringer" and insert --(Boehringer--.

Column 24, line 56, move --ug IgG/well-- to line 51, before "P/N Ratio".

Signed and Sealed this

Twenty-first Day of January, 1997

*Attest:*

BRUCE LEHMAN

*Attesting Officer*  *Commissioner of Patents and Trademarks*